(12) United States Patent
Yeates et al.

(10) Patent No.: US 7,560,411 B2
(45) Date of Patent: Jul. 14, 2009

(54) OLEFIN EPOXIDATION PROCESS, A CATALYST FOR USE IN THE PROCESS, A CARRIER FOR USE IN PREPARING THE CATALYST, AND A PROCESS FOR PREPARING THE CARRIER

(75) Inventors: Randall Clayton Yeates, Sugar Land, TX (US); John Robert Lockemeyer, Sugar Land, TX (US); Marek Matusz, Houston, TX (US)

(73) Assignee: Shell Oil Company, Houston, TX (US)

( * ) Notice: Subject to any disclaimer, the term of this patent is extended or adjusted under 35 U.S.C. 154(b) by 578 days.

(21) Appl. No.: 11/215,267

(22) Filed: Aug. 30, 2005

(65) Prior Publication Data

US 2006/0047130 A1 Mar. 2, 2006

Related U.S. Application Data

(60) Provisional application No. 60/606,193, filed on Sep. 1, 2004.

(51) Int. Cl.
*B01J 23/68* (2006.01)
(52) U.S. Cl. .............. 502/317; 502/324; 502/340; 502/341; 502/347; 502/348; 549/534; 549/536
(58) Field of Classification Search ........... 502/317, 502/324, 340, 347, 208, 218, 341, 348; 549/534, 549/536
See application file for complete search history.

(56) References Cited

U.S. PATENT DOCUMENTS

| | | | | |
|---|---|---|---|---|
| 2,177,361 | A | 10/1939 | Carter | 260/348 |
| 2,209,908 | A | 7/1940 | Weiss | 23/234 |
| 2,294,383 | A | 9/1942 | Carter | 260/348 |
| 3,808,153 | A | 4/1974 | Chomitz et al. | 252/463 |
| 3,950,507 | A | 4/1976 | Kuklina et al. | 423/626 |
| 4,318,896 | A | 3/1982 | Schoonover | 423/628 |
| 4,379,134 | A | 4/1983 | Weber et al. | 423/626 |
| 4,428,863 | A | 1/1984 | Fry | 502/8 |
| 4,477,427 | A | 10/1984 | Mátyasi et al. | 423/628 |
| 4,615,875 | A | 10/1986 | Gonczy et al. | 423/626 |
| 4,731,350 | A | 3/1988 | Boxhoorn et al. | 502/231 |
| 4,742,034 | A | 5/1988 | Boxhoorn et al. | 502/231 |
| 4,761,394 | A | 8/1988 | Lauritzen | 502/348 |
| 4,766,105 | A | 8/1988 | Lauritzen | 502/216 |
| 4,822,900 | A | 4/1989 | Hayden | 549/534 |
| 4,829,044 | A | 5/1989 | Boxhoorn et al. | 502/348 |
| 4,845,296 | A | 7/1989 | Ahmed et al. | 564/477 |
| 4,908,343 | A | 3/1990 | Bhasin | 502/218 |
| 4,994,587 | A | 2/1991 | Notermann et al. | 549/534 |
| 4,994,588 | A | 2/1991 | Kapicak et al. | 549/534 |
| 4,994,589 | A | 2/1991 | Notermann | 549/534 |
| 5,015,614 | A | 5/1991 | Baird, Jr. et al. | 502/250 |
| 5,051,395 | A | 9/1991 | Mitchell et al. | 502/348 |
| 5,063,195 | A | 11/1991 | Jin et al. | 502/341 |
| 5,187,140 | A | 2/1993 | Thorsteinson et al. | 502/348 |
| 5,248,557 | A | 9/1993 | Jacobson | 428/404 |
| 5,380,697 | A | 1/1995 | Matusz et al. | 502/348 |
| 5,538,709 | A | 7/1996 | Mohri et al. | 423/625 |
| 5,612,267 | A | 3/1997 | Bachelard et al. | 501/127 |
| 5,739,075 | A | 4/1998 | Matusz | 502/302 |
| 5,780,656 | A | 7/1998 | Rizkalla et al. | 549/534 |
| 6,203,773 | B1 | 3/2001 | Easley et al. | 423/626 |
| 6,368,998 | B1 | 4/2002 | Lockemeyer | 502/347 |
| 6,667,270 | B2 | 12/2003 | Tanev | 502/208 |
| 2001/0046943 | A1 | 11/2001 | Cheung et al. | 502/325 |
| 2003/0162984 | A1 | 8/2003 | Lockemeyer et al. | 549/534 |
| 2006/0009647 | A1 | 1/2006 | Yeates et al. | 549/534 |
| 2006/0014971 | A1 | 1/2006 | Yeates et al. | 549/534 |
| 2006/0205962 | A1 | 9/2006 | Rubinstein et al. | 549/534 |
| 2006/0258532 | A1 | 11/2006 | Thorsteinson et al. | 502/347 |
| 2007/0111886 | A1 | 5/2007 | Serafin et al. | 502/348 |

FOREIGN PATENT DOCUMENTS

| | | |
|---|---|---|
| CN | 1297884 | 6/2001 |
| CN | 1437590 | 8/2003 |
| EP | 0003642 | 8/1979 |
| EP | 244895 B1 | 11/1987 |
| EP | 0266015 | 5/1988 |
| EP | 266852 A1 | 5/1988 |
| EP | 327356 B1 | 8/1989 |

(Continued)

OTHER PUBLICATIONS

"Kirk-Othmer Encyclopedia of Chemical Technology", 3rd edition, vol. 9, 1980, pp. 445-447.

(Continued)

*Primary Examiner*—Janet L Andres
*Assistant Examiner*—David E Gallis

(57) ABSTRACT

A process is provided for preparing a carrier which process comprises incorporating into the carrier at any stage of the carrier preparation a strength-enhancing additive. Also provided is the resultant carrier having incorporated therein a strength-enhancing additive and a catalyst comprising the carrier. Also provided is a process for the epoxidation of an olefin employing the catalyst. Also provided is a method of using the olefin oxide so produced for making a 1,2-diol, a 1,2-diol ether or an alkanolamine.

19 Claims, No Drawings

FOREIGN PATENT DOCUMENTS

| | | |
|---|---|---|
| EP | 0352850 | 1/1990 |
| EP | 425020 A1 | 5/1991 |
| EP | 429548 B1 | 6/1991 |
| EP | 480537 A1 | 4/1992 |
| EP | 496470 A1 | 7/1992 |
| EP | 679611 A1 | 11/1995 |
| WO | WO9015777 | 12/1990 |
| WO | WO9621619 | 7/1996 |
| WO | 00/15333 | 3/2000 |
| WO | 00/15334 | 3/2000 |
| WO | 00/15335 | 3/2000 |
| WO | WO0119763 A1 | 3/2001 |
| WO | WO2005023418 A1 | 3/2005 |
| WO | WO2006009756 A1 | 1/2006 |
| WO | WO2006028544 A2 | 3/2006 |
| WO | WO2006028940 | 3/2006 |
| WO | WO2006091478 | 8/2006 |

OTHER PUBLICATIONS

Morey, George W., "The Properties of Glass", $2^{nd}$ Edition, American Chemical Society Monograph Series, Reinhold Publishing Corp. (1954), pp. 25, 26, 35.

S. Brunauer, P. H. Emmett & E. Teller, "Adsorption of Gases in Multimolecular Layers" J. of Amer. Chem. Soc., vol. 60 (1938); pp. 309-316.

Supplemental Preliminary Amendment dated Jan. 12, 2007, for U.S. Appl. No. 10/573,694.

Third Supplemental Preliminary Amendment dated Feb. 23, 2007, for U.S. Appl. No. 10/573,694.

Second Supplemental Preliminary Amendment dated Jan. 19, 2007, for U.S. Appl. No. 10/573,694.

Second Supplemental Preliminary Amendment dated Jan. 19, 2007, for U.S. Appl. No. 10/567,178.

Supplemental Preliminary Amendment dated Jan. 12, 2007, for U.S. Appl. No. 10/567,178.

OLEFIN EPOXIDATION PROCESS, A CATALYST FOR USE IN THE PROCESS, A CARRIER FOR USE IN PREPARING THE CATALYST, AND A PROCESS FOR PREPARING THE CARRIER

This application claims the benefit of U.S. Provisional Application No. 60/606,193 filed Sep. 1, 2004, the entire disclosure of which is hereby incorporated by reference.

FIELD OF THE INVENTION

The present invention relates to a process for the production of an olefin oxide, a 1,2-diol, a 1,2-diol ether, or an alkanolamine. The present invention also relates to a catalyst for use in the process for the production of an olefin oxide and a carrier for use in preparing the catalyst. The present invention also relates to a process for preparing the carrier.

BACKGROUND OF THE INVENTION

In olefin epoxidation, a feed containing an olefin and an oxygen source is contacted with a catalyst under epoxidation conditions. The olefin is reacted with oxygen to form an olefin oxide. A product mix results that contains olefin oxide and typically unreacted feed and combustion products, such as carbon dioxide.

The catalyst comprises silver, usually with one or more additional elements deposited therewith, on a carrier, typically an alpha-alumina carrier. The olefin oxide may be reacted with water to form a 1,2-diol, with an alcohol to form a 1,2-diol ether, or with an amine to form an alkanolamine. Thus, 1,2-diols, 1,2-diol ethers, and alkanolamines may be produced in a multi-step process initially comprising olefin epoxidation and then the conversion of the formed olefin oxide with water, an alcohol, or an amine.

The performance of the silver containing catalyst may be assessed on the basis of selectivity, activity, and stability of operation in the olefin epoxidation. The selectivity is the molar fraction of the converted olefin yielding the desired olefin oxide. Stability refers to how the selectivity and/or activity of the process changes during the time a charge of catalyst is being used, i.e., as more olefin oxide is produced.

Various approaches to improving the performance of the silver catalysts, including improvements in selectivity, activity, and stability, have been investigated. For example, modern silver-based catalysts may comprise, in addition to silver, one or more high-selectivity dopants, such as components comprising rhenium, tungsten, chromium, or molybdenum. High-selectivity catalysts are disclosed, for example, in U.S. Pat. No. 4,761,394 and U.S. Pat. No. 4,766,105. U.S. Pat. No. 4,766,105 and U.S. Pat. No. 4,761,394 disclose that rhenium may be employed as a further component in the silver containing catalyst with the effect that the initial, peak selectivity of the olefin epoxidation is increased.

Depending upon the catalyst used and the parameters of the olefin epoxidation process, the time required to reach the initial, peak selectivity, that is the highest selectivity reached in the initial stage of the process, may vary. For example, the initial, peak selectivity of a process may be achieved after only 1 or 2 days of operation or may be achieved after as much as, for example, 1 month of operation. EP-A-352850 also teaches that the then newly developed catalysts, comprising silver supported on alumina carrier, promoted with alkali metal and rhenium components have a very high selectivity.

As another example of an approach to improving the performance of the silver catalysts, fluorine has been incorporated into carriers used to prepare epoxidation catalysts, with an intention that the resultant fluoride-mineralized carriers will have morphological properties conducive to improved catalyst performance. The crush strength or attrition resistance of such fluoride-mineralized carriers, however, can often be inherently lower than desirable. While various additives, often referred to as binders, have been used to improve the crush strength or attrition resistance of carriers, traditional binders typically must be subjected to a high temperature treatment to activate their binding properties. Often, the high temperature treatment involves temperatures in excess of 1,200° C., even in excess 1,300° C. The use of such traditional binders with fluoride-mineralized carriers may not be desirable, as the morphology of the fluoride-mineralized carrier may be detrimentally affected if the carrier is exposed to such high temperatures.

Thus, notwithstanding the improvements already achieved, there is a desire to improve the performance of olefin epoxidation catalysts and, in particular, to increase the crush strength or attrition resistance of fluoride-mineralized carriers without detrimentally affecting the morphology of such carriers.

SUMMARY OF THE INVENTION

The present invention relates to a process for the production of an olefin oxide, a 1,2-diol, a 1,2-diol ether, or an alkanolamine. The present invention also relates to a catalyst for use in the process for the production of olefin oxide and a carrier for use in preparing the catalyst. The present invention also relates to a process for preparing the carrier.

The invention provides a process for increasing the crush strength or attrition resistance of a fluoride-mineralized carrier comprising incorporating into the fluoride-mineralized carrier a strength-enhancing additive. In preferred embodiments, amongst others, the strength-enhancing additive is selected from the group consisting of a zirconium species, a lanthanide Group species, a Group II metal species, an inorganic glass, and mixtures thereof.

The invention also provides a fluoride-mineralized carrier having incorporated therein a strength-enhancing additive. In preferred embodiments, amongst others, the fluoride-mineralized carrier comprises alpha-alumina.

The invention also provides a process for preparing a fluoride-mineralized carrier, which process comprises incorporating into the carrier at any stage of the carrier preparation a strength-enhancing additive.

The invention also provides a catalyst for the epoxidation of an olefin comprising a silver component deposited on a fluoride-mineralized carrier, wherein the fluoride-mineralized carrier has incorporated therein a strength-enhancing additive. In preferred embodiments, amongst others, the catalyst additionally comprises a high-selectivity dopant. In preferred embodiments, amongst others, the catalyst additionally comprises a rhenium component or a rhenium component and rhenium co-promoter. In preferred embodiments, amongst others, the catalyst additionally comprises a Group IA metal component.

The invention also provides a process for the epoxidation of an olefin comprising the steps of contacting a feed comprising an olefin and oxygen with a catalyst comprising a silver component deposited on a fluoride-mineralized carrier and producing a product mix comprising an olefin oxide, wherein the fluoride-mineralized carrier has incorporated therein a strength-enhancing additive. The fluoride-mineralized carrier may have, and preferably does have, a particulate matrix having a morphology characterizable as lamellar or platelet-type, which terms are used interchangeably. As such, particles having in at least one direction a size greater than 0.1 micrometers have at least one substantially flat major surface. Such particles may have two or more flat major surfaces. In alternative embodiments of this invention, the carrier has said platelet-type structure and has been prepared by a method other than the fluoride-mineralization methods described herein.

In preferred embodiments, amongst others, the catalyst additionally comprises a high-selectivity dopant. In preferred embodiments, amongst others, the catalyst additionally comprises a rhenium component or a rhenium component and a rhenium co-promoter. In preferred embodiments, amongst others, the catalyst additionally comprises a Group IA metal component. In preferred embodiments, amongst others, the process exhibits a selectivity to the olefin oxide greater than 85%, preferably greater than 87%, more preferably greater than about 89%, and even more preferably greater than about 90% and frequently as much as about 92%.

The invention also provides a process for the production of a 1,2-diol, a 1,2-diol ether, or an alkanolamine comprising converting an olefin oxide into the 1,2-diol, the 1,2-diol ether, or the alkanolamine, wherein the olefin oxide has been obtained by a process for the epoxidation of an olefin comprising reacting the olefin with oxygen in accordance with this invention.

It is envisioned that catalysts comprising the carrier of this invention and an amount of an appropriate catalytic species, frequently a metallic species such as silver, molybdenum, nickel, and tungsten, or compounds thereof, may advantageously be employed in other conversion processes.

The features and advantages of the present invention will be readily apparent to those skilled in the art upon reading the description of the invention that follows.

DETAILED DESCRIPTION OF THE INVENTION

The present invention relates to a process for the production of an olefin oxide, a 1,2-diol, a 1,2-diol ether, or an alkanolamine. The present invention also relates to a catalyst for use in the process for the production of an olefin oxide and a carrier for use in preparing the catalyst. The present invention also relates to a process for preparing the carrier.

The invention provides a process for increasing the crush strength or attrition resistance of a fluoride-mineralized carrier in which a strength-enhancing additive is incorporated into the fluoride-mineralized carrier. The invention also provides a catalyst for the epoxidation of an olefin comprising a silver component deposited on a fluoride-mineralized carrier, wherein the fluoride-mineralized carrier has incorporated therein a strength-enhancing additive. The invention also provides a process for the epoxidation of an olefin comprising the steps of contacting a feed comprising an olefin and oxygen with a catalyst comprising a silver component deposited on a fluoride-mineralized carrier and producing a product mix comprising an olefin oxide, wherein the fluoride-mineralized carrier has incorporated therein a strength-enhancing additive.

Fluoride-Mineralized Carrier

Fluoride-mineralized carriers are obtained by the incorporation of fluorine into the carrier. For purposes of the present invention, fluoride-mineralized carriers are obtained by combining alpha-alumina or alpha-alumina precursor(s) with a fluorine-containing species that is capable of liberating fluoride, typically as hydrogen fluoride, when the combination is calcined, and calcining the combination. Prior to calcining, the combination may be formed into formed bodies, for example by extrusion or spraying. Preferably, calcination is conducted at less than about 1,200° C., more preferably at less than about 1,100° C. Preferably, calcination is conducted at greater than about 900° C., more preferably at greater than about 1,000° C. If the temperature is sufficiently in excess of 1,200° C., the amount of fluoride liberated may be excessive and the morphology of the carrier may be detrimentally affected.

The manner by which the fluorine-containing species is introduced into the carrier is not limited, and those methods known in the art for incorporating a fluorine-containing species into a carrier, and those fluoride-mineralized carriers obtained therefrom, may be used for the present invention. For example, U.S. Pat. No. 3,950,507 and U.S. Pat. No. 4,379,134 disclose methods for preparing fluoride-mineralized carriers and are hereby incorporated by reference.

As indicated hereinbefore, the fluoride-mineralized carriers may have, and preferably do have, a particulate matrix having a morphology characterizable as lamellar or platelet-type, which terms are used interchangeably. As such, particles having in at least one direction a size greater than about 0.1 micrometers have at least one substantially flat major surface. Such particles may have two or more flat major surfaces. In alternative embodiments of this invention, carriers may be used which have said platelet-type structure and which have been prepared by a method other than the fluoride-mineralization methods described herein.

A suitable procedure for incorporating a fluorine-containing species into a carrier involves adding a fluorine-containing species to alpha-alumina or an alpha-alumina precursor (s). The alpha-alumina precursors mentioned herein are those species capable of being converted to alpha-alumina upon calcination. The alpha-alumina precursors include hydrated aluminas, such as boehmite, pseudoboehmite, and gibbsite, as well as transition aluminas, such as the chi, kappa, gamma, delta, theta, and eta aluminas.

If a hydrated alumina is used, a fluorine-containing species suitably may be added to the hydrated alumina with the combination then made into formed bodies, such as by extrusion or spraying. The hydrated alumina is then converted to alpha-alumina by calcining the formed bodies. Preferably, the calcination is conducted at less than about 1,200° C. During the calcination, fluoride is liberated. Similarly, a fluorine-containing species suitably may be added to a transition alumina, such as gamma alumina, or to a combination of transition alumina and hydrated alumina. The combination is made into formed bodies and calcined, as before.

In another suitable method, a fluorine-containing species may be added to formed bodies of alpha-alumina or an alpha-alumina precursor(s) or mixtures thereof. The formed bodies are then subjected to calcination. In another suitable method, the fluorine-containing species may be added to the carrier after calcination, i.e., after formation of alpha-alumina. In such a method, the fluorine-containing species may be conveniently incorporated in the same manner as silver and any other promoters, e.g., by impregnation, typically vacuum impregnation.

As previously explained, calcination is preferably conducted at less than about 1,200° C. The present invention, however, is independent of the manner by which calcination is conducted. Thus, variations in calcining known in the art, such as holding at one temperature for a certain period of time and then raising the temperature to a second temperature over the course of a second period of time, are contemplated by the present invention.

The addition of the fluorine-containing species may be by any known method. In one such suitable method, the alpha-alumina or alpha-alumina precursor(s) is treated with a solution containing a fluorine-containing species. The combination is co-mulled and extruded. Similarly, formed bodies may be subjected to vacuum impregnation with a solution containing a fluorine-containing species. Any combination of solvent and fluorine-containing species that results in the presence of fluoride ions in solution may be used in accordance with such a method.

Fluorine-containing species that may be used in accordance with this invention are those species that when incorporated into a carrier in accordance with this invention are capable of liberating fluoride, typically in the form of hydrogen fluoride, when calcined, preferably at less than about 1,200° C. Preferred fluorine-containing species are capable of liberating fluoride when calcining is conducted at a temperature of from about 900° C. to about 1,200° C. Such fluorine-containing species known in the art may be used in accordance with this invention. Suitable fluorine-containing species include organic and inorganic species. Suitable fluorine-containing species include ionic, covalent, and polar covalent compounds. Suitable fluorine-containing species include $F_2$, aluminum trifluoride, ammonium fluoride, hydrofluoric acid, and dichlorodifluoromethane.

Typically, the amount of fluorine-containing species added to the carrier is at least about 0.1 percent by weight and typically no greater than about 5 percent by weight, calculated as the weight of elemental fluorine used relative to the weight of the carrier material to which the fluorine-containing species is being incorporated. Frequently, the fluorine-containing species is used in an amount from about 0.2 to about 3 percent by weight. More frequently, the fluorine-containing species is used in an amount from about 0.25 to about 2.5 percent by weight. These amounts refer to the amount of the species as initially added and do not necessarily reflect the amount that may ultimately be present in the finished carrier.

An advantage of the present invention is that the fluoride-mineralized carriers, or carriers having a particulate matrix having a lamellar or platelet-type morphology, have incorporated therein an additive that serves to increase the crush strength or attrition resistance of the carrier. Strength-enhancing additives are those species that when incorporated into the carrier result in an increase in the crush strength or improvement in the attrition resistance of the carrier. Suitably, the strength-enhancing additives are easily incorporated into the alumina crystal structure of the carrier, for example into the alumina crystal structure of a fluoride-mineralized carrier, by calcination at temperatures less than about 1,200° C., more preferably at less than about 1,100° C. Frequently, the strength-enhancing additives are easily incorporated into the alumina crystal structure of the carrier by calcination at temperatures greater than about 900° C., more frequently at greater than about 1,000° C. Preferably, the strength-enhancing additive is capable of forming fluoride species, typically having a relatively low volatility so as to enhance their interaction with the carrier leading to the strength-enhancing effect. Strength-enhancing additives may be selected from the group consisting of a zirconium species, a lanthanide Group species, a Group II metal species, an inorganic glass, and mixtures thereof.

The specific form in which the strength-enhancing additive exists prior to being incorporated into the carrier is not limited. Thus, zirconium species, a lanthanide Group species, and Group II metal species includes any specific element as such and compounds of the element. Illustrative strength-enhancing additives include ammonium fluorozirconate, calcium zirconate, zirconium acetate, zirconium acetylacetonate, zirconium carbonate, zirconium fluoride, zirconium oxynitrate, zirconium silicate, lanthanum carbonate, lanthanum fluoride, lanthanum nitrate, lanthanum oxalate, lanthanum oxide, cerium carbonate, cerium fluoride, cerium nitrate, cerium oxalate, cerium oxide, magnesium acetate, magnesium carbonate, magnesium fluoride, magnesium nitrate, magnesium oxalate, magnesium oxide, calcium acetate, calcium carbonate, calcium fluoride, calcium nitrate, calcium oxalate, and calcium oxide.

Preferably, the inorganic glass has a melting temperature that is at most the temperature at which the calcination is carried out. For example, the inorganic glass may have a melting temperature that is below 1,200 ° C. Melting temperature of the inorganic glass is understood to mean the temperature at which the ingredients of the inorganic glass would be heated during glass manufacture to obtain a fluid. Typical inorganic glass compositions may include the elements silicon, boron, aluminum, or lead in combination with many other elements, such as alkali and alkaline earth metals. These elements are typically employed as their oxides. Illustrative inorganic glass compositions that may be used for purposes of the present invention include, among many others, the following: $Na_2O.SiO_2+Na_2O.2SiO_2$, $Na_2O.2SiO_2+SiO_2$ (quartz), $K_2O.SiO_2+K_2O.2SiO_2$, $K_2O.2SiO_2+K_2O.4SiO_2$, $PbO$, $2PbO.SiO_2+PbO.SiO_2$, $Na_2O.SiO_2+Na_2O.2SiO_2+2Na_2O.CaO.3SiO_2$, $K_2O.2SiO_2+K_2O.2CaO.9SiO_2+K_2O.4SiO_2$, $Na_2O.4B_2O_3+SiO_2$, and $Na_2O.2B_2O_3+Na_2O.SiO_2$.

Within these limitations, the manner by which the strength-enhancing additive is incorporated into the carrier is not generally limited. Similarly, the point in the process for preparing the carrier when the strength-enhancing additive is incorporated is not generally limited. Indeed, it is expected that, depending on the specific strength-enhancing additive or combination thereof used as well as the amount of the strength-enhancing additive used, those methods used to incorporate fluorine-containing species into the carrier as well as other methods may be suitably used to incorporate the strength-enhancing additive. For example, in one such suitable method, the alpha-alumina or alpha-alumina precursor(s) is combined with a strength-enhancing additive, such as calcium acetate. The strength-enhancing additive may be used in the form of a composition comprising the strength-enhancing additive, for example as a solution or as a dispersion in a diluent, suitably an aqueous diluent or, less preferred, an organic diluent. The strength-enhancing additive may be added simultaneously with the fluorine-containing species; however, the fluorine-containing species may have been added previously or may be added subsequently. After the alpha-alumina or alpha-alumina precursor(s) is combined with the strength-enhancing additive, the combination may be co-mulled and made into formed bodies and subsequently calcined. Similarly, an extrudate or other formed bodies may be combined with the strength-enhancing additive, for example by subjecting the formed bodies to impregnation or vacuum impregnation with a solution or emulsion containing the strength-enhancing additive, and subsequently calcined. When inorganic glass is used as the strength-enhancing additive, ground inorganic glass or the individual components of the desired inorganic glass may be combined with alpha-alumina or alpha-alumina precursor(s), with the combination then being heated and made into formed bodies. The inorganic glass may be introduced in other manners. For example, in certain embodiments, the individual components of the inorganic glass may be introduced as a solution in a solvent.

As indicated above, the present invention does not contemplate that the strength-enhancing additive must be incorporated into the carrier simultaneously with the fluorine-containing species. The present invention contemplates that the strength-enhancing additive may be incorporated simultaneously, before, or after the fluorine-containing species. Suitable methods to incorporate the strength-enhancing additive as well as suitable points during the process for preparing the carrier when the strength-enhancing additive is incorporated may be selected on the basis of routine experimentation.

For purposes of the present invention, a strength-enhancing additive may, for example, suitably be added to hydrated alumina, such as boehmite, with the combination then made into formed bodies and calcined, as before. Similarly, a strength-enhancing additive may suitably be added to a transition alumina, such as gamma alumina, or to a combination of transition alumina and hydrated alumina. The combination is made into formed bodies, for example by extrusion or spraying, and calcined, as before. In another suitable method, a strength-enhancing additive may be added to formed bodies of alpha-alumina or an alpha-alumina precursor(s) or mixtures thereof. The formed bodies are then subjected to calcination. In another suitable method, the strength-enhancing additive may be added to a carrier having a particulate matrix having a lamellar or platelet-type morphology, i.e., after formation of alpha-alumina, and calcined. In such a method, the strength-enhancing additive may be conveniently incorporated in the same manner as silver and any other promoters, e.g., by impregnation, typically vacuum impregnation.

The determination of an appropriate strength-enhancing amount of any specific strength-enhancing additive or combination of strength-enhancing additives for use in this invention is a matter of routine experimentation. Suitably, it is desirable to conduct range-finding experiments to determine the strength-enhancing amount range for any specific strength-enhancing additive or combination of additives. A fluoride-mineralized carrier, or a carrier having a particulate matrix having a lamellar or platelet-type morphology, containing no strength-enhancing additive is desirably prepared to provide a basis of comparison. Any lower or upper concentration limit for a specific strength-enhancing additive or combination thereof may thereafter be determined by preparing a series of carriers containing successively larger amounts of the strength-enhancing additive or combination thereof. The experiments will typically be continued until the measured crush strength or attrition resistance of the last carrier is inferior to that of the preceding carrier. The specific response of any strength-enhancing additive or combination thereof may be further refined, if desired, by conducting additional experiments with intermediate amounts of the strength-enhancing additive or combination thereof.

While not being limited, it is expected that, typically, the strength-enhancing amount of strength-enhancing additive will for zirconium species be at least about 0.1 percent by weight, frequently at least about 0.2 percent by weight, more frequently at least about 0.5 percent by weight, even more frequently at least about 1 percent by weight, and no greater than about 5 percent by weight, frequently no greater than about 4 percent by weight, calculated as the weight of the element zirconium used relative to the total weight of the carrier. While not being limited, it is expected that, typically, the strength-enhancing amount of strength-enhancing additive will for lanthanide Group species be at least about 0.1 percent by weight, frequently at least about 0.2 percent by weight, more frequently at least about 0.5 percent by weight, even more frequently at least about 1 percent by weight, and no greater than about 5 percent by weight, frequently no greater than about 4 percent by weight, calculated as the weight of the lanthanide Group element used relative to the total weight of the carrier. While not being limited, it is expected that, typically, the strength-enhancing amount of strength-enhancing additive will for Group II metal species be at least about 0.1 percent by weight, frequently 0.2 percent by weight, more frequently at least about 0.5 percent by weight, even more frequently at least about 1 percent by weight, and no greater than about 5 percent by weight, frequently no greater than about 4 percent by weight, calculated as the weight of the Group II metal element used relative to the total weight of the carrier. While not being limited, it is expected that, typically, the strength-enhancing amount of strength-enhancing additive will for inorganic glass be at least about 0.1 percent by weight, frequently at least about 0.2 percent by weight, more frequently at least about 0.5 percent by weight, even more frequently at least about 1 percent by weight, and no greater than about 5 percent by weight, frequently no greater than about 4 percent by weight, calculated as the weight of inorganic glass used relative to the total weight of the carrier. These amounts refer to the amount of the additive as initially added and do not necessarily reflect the amount that may ultimately be present in the finished carrier.

For purposes of the present invention, the crush strength of a carrier or the attrition resistance of a carrier can be measured in a number of ways. A suitable way to measure crush strength is using ASTM D6175-03. A suitable way to measure attrition resistance is using ASTM D4058-96. By use of these ASTM methods or other methods for testing crush strength or attrition resistance, a carrier having incorporated therein a certain amount of a strength-enhancing additive may be compared to other carriers having a different strength-enhancing additive or a different amount of the same strength-enhancing additive. Comparisons may also be made to a comparable carrier that does not have incorporated therein a strength-enhancing additive. Thus, a carrier having incorporated therein a strength-enhancing amount of a strength-enhancing additive can be obtained. In certain embodiments, it is desirable to employ a strength enhancing additive in amounts sufficient to achieve a carrier having a practical crush strength or practical attrition resistance for use in the commercial production of olefin oxide. Suitably, the fluoride-mineralized carrier or the carrier having the lamellar or platelet-type morphology has a crush strength of at least about 0.4 pound-force per millimeter (lbf/mm) (approximately 1.8 N/mm), preferably at least about 2 N/mm, more preferably at least about 3.5 N/mm, even more preferably at least about 5 N/mm and frequently as much as about 40 N/mm, more frequently as much as about 25 N/mm, even more frequently as much as about 15 N/mm. Such crush strengths are measured in accordance with ASTM D6175-03, wherein the test sample is tested as such after its preparation, that is with elimination of Step 7.2 of said method, which represents a step of drying the test sample. For this crush strength test method, the crush strength of a formed carrier is typically measured as the crush strength of hollow cylindrical particles of 8.8 mm external diameter, 3.5 mm internal diameter, and 8 mm length.

Attrition resistance, as used herein, is measured in accordance with ASTM D4058-96, wherein the test sample is tested as such after its preparation, that is with elimination of Step 6.4 of the said method, which represents a step of drying the test sample. Preferably, the fluoride-mineralized carrier or the carrier having the lamellar or platelet-type morphology exhibits, when in shaped form, in particular in the form of hollow cylindrical particles of 8.8 mm external diameter, 3.5 mm internal diameter and 8 mm length, attrition of at most 50 percent, more preferably at most 40 percent, in particular at most 30 percent. Frequently, the attrition may be at least 10 percent, in particular at least 15%, more in particular at least 20 percent.

When the shaped carrier is present in a particular shape other than the hollow cylinders as defined, the crush strength or attrition resistance may be measured by repeating the preparation of the shaped carrier with the difference that the carrier is shaped into the hollow cylinders as defined, instead of the particular shape, and the crush strength or attrition resistance of the hollow cylinders so obtained is measured.

Other than being as described above, the carriers that may be used in accordance with this invention are not generally limited. Typically, suitable carriers comprise at least 85 percent by weight, more typically 90 percent by weight, in particular 95 percent by weight alpha-alumina, frequently up to 99.9 percent by weight alpha-alumina, based on the weight of the carrier. The carrier may additionally comprise, silica, alkali metal, for example sodium and/or potassium, and/or alkaline earth metal, for example calcium and/or magnesium.

Suitable carriers generally are also not limited with respect to surface area, water absorption, or other properties. However, it will be understood by those skilled in the art that surface area, water absorption, and other properties can affect the crush strength or attrition resistance of the carrier. The surface area of the carrier may suitably be at least 0.1 $m^2/g$, preferably at least 0.3 $m^2/g$, more preferably at least 0.5 $m^2/g$, and in particular at least 0.6 $m^2/g$, relative to the weight of the carrier; and the surface area may suitably be at most 10 $m^2/g$, preferably at most 5 $m^2/g$, and in particular at most 3 $m^2/g$, relative to the weight of the carrier. "Surface area" as used herein is understood to relate to the surface area as determined by the B.E.T. (Brunauer, Emmett and Teller) method as described in Journal of the American Chemical Society 60 (1938) pp. 309-316. High surface area carriers, in particular when they are alpha-alumina carriers optionally comprising in addition silica, alkali metal and/or alkaline earth metal, provide improved performance and stability of operation. However, when the surface area is very large, carriers tend to have lower crush strength or attrition resistance.

The water absorption of the carrier may suitably be in the range of from 0.2 to 0.8 g/g, preferably in the range of from 0.3 to 0.7 g/g, relative to the weight of the carrier. A higher water absorption may be in favor in view of a more efficient deposition of silver and further elements, if any, on the carrier by impregnation. However, at higher water absorptions, the carrier, or the catalyst made therefrom, may have lower crush strength or attrition resistance. As used herein, water absorption is deemed to have been measured in accordance with ASTM C20, and water absorption is expressed as the weight of the water that can be absorbed into the pores of the carrier, relative to the weight of the carrier.

Catalyst

In accordance with the present invention, the catalyst may comprise a silver component deposited on the previously described carrier having incorporated therein a strength-enhancing amount of a strength-enhancing additive.

The catalyst comprises silver as a catalytically active component. Appreciable catalytic activity is typically obtained by employing silver in an amount of at least 10 g/kg, calculated as the weight of the element relative to the weight of the catalyst. Preferably, the catalyst comprises silver in a quantity of from 50 to 500 g/kg, more preferably from 100 to 400 g/kg, for example 105 g/kg, or 120 g/kg, or 190 g/kg, or 250 g/kg, or 350 g/kg.

The catalyst may comprise, in addition to silver, one or more high-selectivity dopants. Catalysts comprising a high-selectivity dopant are known from U.S. Pat. No. 4,761,394 and U.S. Pat. No. 4,766,105, which are incorporated herein by reference. The high-selectivity dopants may comprise, for example, components comprising one or more of rhenium, molybdenum, chromium, tungsten, and nitrate- or nitrite-forming compounds. The high-selectivity dopants may each be present in a quantity of from 0.01 to 500 mmole/kg, calculated as the element (for example, rhenium, molybdenum, tungsten, nitrogen, and/or chromium) on the total catalyst. The nitrate- or nitrite-forming compounds and particular selections of nitrate- or nitrite-forming compounds are as defined hereinafter. The nitrate- or nitrite-forming compound is in particular a Group IA metal nitrate or a Group IA metal nitrite. Rhenium, molybdenum, chromium, tungsten, or the nitrate- or nitrite-forming compound may suitably be provided as an oxide or as an oxyanion, for example, as a perrhenate, molybdate, tungstate, or nitrate in salt or acid form. The high-selectivity dopants may be employed in the preparation of the catalyst in a quantity sufficient to provide a catalyst having a content of high-selectivity dopant as disclosed herein.

Of special preference are catalysts that comprise a rhenium component, and more preferably also a rhenium co-promoter, in addition to silver. Rhenium co-promoters are selected from tungsten, molybdenum, chromium, sulfur, phosphorus, boron, compounds thereof, and mixtures thereof.

When the catalyst comprises a rhenium component, rhenium may typically be present in a quantity of at least 0.1 mmole/kg, more typically at least 0.5 mmole/kg, and preferably at least 1 mmole/kg, in particular at least 1.5 mmole/kg, calculated as the quantity of the element relative to the weight of the catalyst. Rhenium is typically present in a quantity of at most 5 mmole/kg, preferably at most 3 mmole/kg, more preferably at most 2 mmole/kg, in particular at most 1.5 mmole/kg. Again, the form in which rhenium is provided to the carrier is not material to the invention. For example, rhenium may suitably be provided as an oxide or as an oxyanion, for example, as a rhenate or perrhenate, in salt or acid form.

If present, typical amounts of the rhenium co-promoter are from 0.1 to 30 mmole/kg, based on the total amount of the relevant elements, i.e., tungsten, molybdenum, chromium, sulfur, phosphorus and/or boron, relative to the weight of the catalyst. The form in which the rhenium co-promoter is provided to the carrier is not material to the invention. For example, the rhenium co-promoter may suitably be provided as an oxide or as an oxyanion, in salt or acid form.

Suitably, the catalyst may also comprise a Group IA metal component. The Group IA metal component typically comprises one or more of lithium, potassium, rubidium, and cesium. Preferably the Group IA metal component is lithium, potassium and/or cesium. Most preferably, the Group IA metal component comprises cesium or cesium in combination with lithium. Typically, the Group IA metal component is present in the catalyst in a quantity of from 0.01 to 100 mmole/kg, more typically from 0.50 to 50 mmole/kg, more typically from 1 to 20 mmole/kg, calculated as the total quantity of the element relative to the weight of the catalyst. The form in which the Group IA metal is provided to the carrier is not material to the invention. For example, the Group IA metal may suitably be provided as a hydroxide or salt.

As used herein, the quantity of Group IA metal present in the catalyst is deemed to be the quantity in so far as it can be extracted from the catalyst with de-ionized water at 100° C. The extraction method involves extracting a 10-gram sample of the catalyst three times by heating it in 20 mL portions of de-ionized water for 5 minutes at 100° C. and determining in the combined extracts the relevant metals by using a known method, for example atomic absorption spectroscopy.

The preparation of the catalysts, including methods for incorporating silver, high-selectivity dopant, and Group IA metal is known in the art and the known methods are applicable to the preparation of the catalyst that may be used in accordance with the present invention. Methods of preparing the catalyst include impregnating the carrier with a silver compound and performing a reduction to form metallic silver particles. Reference may be made, for example, to U.S. Pat. No. 5,380,697, U.S. Pat. No. 5,739,075, EP-A-266015, U.S. Pat. No. 6,368,998, WO-00/15333, WO-00/15334 and WO-00/15335, which are incorporated herein by reference.

The reduction of cationic silver to metallic silver may be accomplished during a step in which the catalyst is dried, so that the reduction as such does not require a separate process step. This may be the case if the impregnation solution comprises a reducing agent, for example, an oxalate. Such a drying step is suitably carried out at a temperature of at most 600° C., preferably at most 300° C., more preferably at most 280° C., even more preferably at most 260° C., and suitably at a temperature of at least 100° C., preferably at least 200° C., more preferably at least 210° C., even more preferably at least 220° C., suitably for a period of time of at least 1 minute, preferably at least 2 minutes, and suitably for a period of time of at most 60 minutes, preferably at most 20 minutes, more preferably at most 15 minutes, and more preferably at most 10 minutes.

Epoxidation Process

Although the present epoxidation process may be carried out in many ways, it is desirable to carry it out as a gas phase process, i.e., a process in which the feed is contacted in the gas phase with the catalyst which is present as a solid material, typically in a fixed bed under epoxidation conditions. Epoxidation conditions are those combinations of conditions, notably temperature and pressure, under which epoxidation will occur. Generally the process is carried out as a continuous process, such as the typical commercial process involving fixed-bed, tubular reactors.

The typical commercial reactor has a plurality of elongated tubes typically situated parallel to each other. While the size and number of tubes may vary from reactor to reactor, a typical tube used in a commercial reactor will have a length between 4-15 meters and an internal diameter between 1-7 centimeters. Suitably, the internal diameter is sufficient to accommodate the catalyst. In particular, the internal diameter of the tube is sufficient to accommodate the formed bodies of the carrier. Frequently, in commercial scale operation, the process of the invention may involve a quantity of catalyst which is at least 10 kg, for example at least 20 kg, frequently in the range of from $10^2$ to $10^7$ kg, more frequently in the range of from $10^3$ to $10^6$ kg.

The olefin used in the present epoxidation process may be any olefin, such as an aromatic olefin, for example styrene, or a di-olefin, whether conjugated or not, for example 1,9-decadiene or 1,3-butadiene. Mixtures of olefins may be used. Typically, the olefin is a mono-olefin, for example 2-butene or isobutene. Preferably, the olefin is a mono-α-olefin, for example 1-butene or propylene. The most preferred olefin is ethylene.

The olefin concentration in the feed may be selected within a wide range. Typically, the olefin concentration in the feed will be at most 80 mole-%, relative to the total feed. Desirably, it will be in the range of from 0.5 to 70 mole-%, in particular from 1 to 60 mole-%, on the same basis. As used herein, the feed is considered to be the composition that is contacted with the catalyst.

The present epoxidation process may be air-based or oxygen-based, see "Kirk-Othmer Encyclopedia of Chemical Technology", $3^{rd}$ edition, Volume 9, 1980, pp. 445-447. In the air-based process, air or air enriched with oxygen is employed as the source of the oxidizing agent while in the oxygen-based processes high-purity (typically at least 95 mole-%) oxygen is employed as the source of the oxidizing agent. Presently, most epoxidation plants are oxygen-based and this is a preferred embodiment of the present invention.

The oxygen concentration in the feed may be selected within a wide range. However, in practice, oxygen is generally applied at a concentration that avoids the flammable regime. Typically, the concentration of oxygen applied will be within the range of from 1 to 15 mole-%, more typically from 2 to 12 mole-% of the total feed.

In order to remain outside the flammable regime, the concentration of oxygen in the feed may be lowered as the concentration of the olefin is increased. The actual safe operating ranges depend, along with the feed composition, on the reaction conditions such as the reaction temperature and the pressure.

A reaction modifier may be present in the feed for increasing the selectivity, suppressing the undesirable oxidation of olefin or olefin oxide to carbon dioxide and water, relative to the desired formation of olefin oxide. Many organic compounds, especially organic halides and organic nitrogen compounds, may be employed as the reaction modifier. Nitrogen oxides, hydrazine, hydroxylamine or ammonia may be employed as well. It is frequently considered that under the operating conditions of olefin epoxidation the nitrogen containing reaction modifiers are precursors of nitrates or nitrites, i.e. they are so-called nitrate- or nitrite-forming compounds (cf. e.g. EP-A-3642 and U.S. Pat. No. 4,822,900, which are incorporated herein by reference).

Organic halides are the preferred reaction modifiers, in particular organic bromides, and more in particular organic chlorides. Preferred organic halides are chlorohydrocarbons or bromohydrocarbons. More preferably they are selected from the group of methyl chloride, ethyl chloride, ethylene dichloride, ethylene dibromide, vinyl chloride or a mixture thereof. Most preferred reaction modifiers are ethyl chloride and ethylene dichloride.

Suitable nitrogen oxides are of the general formula $NO_x$ wherein x is in the range of from 1 to 2, and include for example NO, $N_2O_3$ and $N_2O_4$. Suitable organic nitrogen compounds are nitro compounds, nitroso compounds, amines, nitrates and nitrites, for example nitromethane, 1-nitropropane or 2-nitropropane. In preferred embodiments, nitrate- or nitrite-forming compounds, e.g. nitrogen oxides and/or organic nitrogen compounds, are used together with an organic halide, in particular an organic chloride.

The reaction modifiers are generally effective when used in low concentration in the feed, for example up to 0.1 mole-%, relative to the total feed, for example from $0.01 \times 10^{-4}$ to 0.01 mole-%. In particular when the olefin is ethylene, it is preferred that the reaction modifier is present in the feed at a concentration of from $0.1 \times 10^{-4}$ to $50 \times 10^{-4}$ mole-%, in particular from $0.3 \times 10^{-4}$ to $30 \times 10^{-4}$ mole-%, relative to the total feed.

In addition to the olefin, oxygen, and the reaction modifier, the feed may contain one or more optional components, for example inert gases and saturated hydrocarbons. Inert gases, for example nitrogen or argon, may be present in the feed in a concentration of from 30 to 90 mole-%, typically from 40 to 80 mole-%, relative to the total feed. The feed may contain saturated hydrocarbons. Suitable saturated hydrocarbons are methane and ethane. If saturated hydrocarbons are present, they may be present in a quantity of up to 80 mole-%, relative to the total feed, in particular up to 75 mole-%. Frequently they may be present in a quantity of at least 30 mole-%, more frequently at least 40 mole-%. Saturated hydrocarbons may be added to the feed in order to increase the oxygen flammability limit.

The epoxidation process may be carried out using epoxidation conditions, including temperature and pressure, selected from a wide range. Preferably the reaction temperature is in the range of from 150 to 340° C., more preferably in the range of from 180 to 325° C. The reaction temperature may be increased gradually or in a plurality of steps, for example in steps of from 0.1 to 20° C., in particular 0.2 to 10° C., more in particular 0.5 to 5° C. The total increase in the reaction temperature may be in the range of from 10 to 140° C., more typically from 20 to 100° C. The reaction temperature may be increased typically from a level in the range of from 150 to 300° C., more typically from 200 to 280° C., when a fresh catalyst is used, to a level in the range of from 230 to 340° C., more typically from 240 to 325° C., when the catalyst has decreased in activity due to ageing.

The epoxidation process is typically carried out at a reactor inlet pressure in the range of from 1,000 to 3,500 kPa. "GHSV" or Gas Hourly Space Velocity is the unit volume of gas at normal temperature and pressure (0° C., 1 atm, i.e., 101.3 kPa) passing over one unit volume of packed catalyst per hour. Preferably, when the epoxidation process is a gas phase process involving a fixed catalyst bed, the GHSV is in the range of from 1500 to 10000 Nl/(l.h).

Carbon dioxide is a by-product in the epoxidation process, and thus may be present in the feed. The carbon dioxide may be present in the feed as a result of being recovered from the product mix together with unconverted olefin and/or oxygen and recycled. Typically, a concentration of carbon dioxide in the feed in excess of 25 mole-%, preferably in excess of 10 mole-%, relative to the total feed, is avoided.

An advantage of the present invention is that when the process is conducted at lower levels of carbon dioxide in the feed and the catalyst comprises a rhenium component, the process exhibits high peak selectivity and improved stability, including improved stability in selectivity and/or improved stability in activity. As such, the process of the present invention is desirably conducted under conditions where the concentration of carbon dioxide in the feed is lower than about 2 mole-%, relative to the total feed. Suitably, a concentration of carbon dioxide lower than about 1 mole-%, in particular lower than about 0.75 mole-%, is used. Frequently, when practicing the present invention, the concentration of carbon dioxide is at least 0.1 mole-%, and more frequently the concentration of carbon dioxide is at least 0.3 mole-%. A concentration of carbon dioxide between about 0.50 mole-% and 0.75 mole-% is particularly desirable. It is contemplated that the process of the present invention may be conducted at nominal concentrations of carbon dioxide in the feed, i.e., concentrations approaching if not reaching zero mole-%. Indeed, a process conducted in the absence of carbon dioxide in the feed is within the scope of the present invention.

Catalyst performance is conveniently measured using a standard set of procedures and process conditions. For example, a typical standard procedure calls for 3.9 g of crushed catalyst to be loaded into a stainless steel U-shaped tube. The tube is then immersed in a molten metal bath (heat medium) and the ends connected to a gas flow system. The weight of catalyst used and the inlet gas flow rate are adjusted to give a gas hourly space velocity of 3,300 Nl/(l.h), as calculated for uncrushed catalyst. The gas flow is then adjusted to 16.9 Nl/h with an inlet gas pressure of 1,370 kPa. The gas mixture passed through the catalyst bed, in a "once-through" operation, during the entire test run including the start-up, is conveniently set at 30% v ethylene, 8% v oxygen, 0.5% v carbon dioxide, 61.5% v nitrogen and 2.0 to 6.0 parts by million by volume (ppmv) ethyl chloride. The initial reactor temperature is conveniently 180° C. and is ramped up at a rate of about 10° C. per hour to 225° C. and then adjusted so as to achieve a desired partial pressure of 41 kPa of ethylene oxide at the reactor outlet.

When operating at these operating conditions, the olefin epoxidation process using a catalyst comprising a silver component and a rhenium component deposited on a fluoride-mineralized carrier, or carrier having a particulate matrix having a lamellar or platelet-type morphology, having incorporated therein a strength-enhancing amount of a strength-enhancing additive, can achieve peak selectivities greater than 85%. Preferably, the process achieves peak selectivities greater than 87%. More preferably, the process achieves peak selectivities greater than 89% and even greater than 90%. Frequently, the process achieves peak selectivities of at most about 92%.

Additionally, when operating at these levels of carbon dioxide in the feed, the olefin epoxidation process using a catalyst comprising a silver component and a rhenium component deposited on the carrier, having incorporated therein a strength-enhancing amount of a strength-enhancing additive, achieves improved stability.

The olefin oxide produced may be recovered from the product mix by using methods known in the art, for example by absorbing the olefin oxide from a product mix in water and optionally recovering the olefin oxide from the aqueous solution by distillation. At least a portion of the aqueous solution containing the olefin oxide may be applied in a subsequent process for converting the olefin oxide into a 1,2-diol, a 1,2-diol ether, or an alkanolamine. The methods employed for such conversions are not limited, and those methods known in the art may be employed. The term "product mix" as used herein is understood to refer to the product recovered from the outlet of the epoxidation reactor.

The conversion into the 1,2-diol or the 1,2-diol ether may comprise, for example, reacting the olefin oxide with water, suitably using an acidic or a basic catalyst. For example, for making predominantly the 1,2-diol and less 1,2-diol ether, the olefin oxide may be reacted with a ten fold molar excess of water, in a liquid phase reaction in the presence of an acid catalyst, e.g., 0.5-1.0% w sulfuric acid, based on the total reaction mixture, at 50-70° C. at 1 bar absolute, or in a gas phase reaction at 130-240° C. and 20-40 bar absolute, preferably in the absence of a catalyst. If the proportion of water is lowered the proportion of 1,2-diol ethers is increased. The 1,2-diol ethers thus produced may be a di-ether, tri-ether, tetra-ether or a subsequent ether. Alternatively, 1,2-diol ethers may be prepared by converting the olefin oxide with an alcohol, in particular a primary alcohol, such as methanol or ethanol, by replacing at least a portion of the water by the alcohol.

The conversion into the alkanolamine may comprise reacting the olefin oxide with an amine, such as ammonia, an alkyl amine, or a dialkylamine. Anhydrous or aqueous ammonia may be used. Anhydrous ammonia is typically used to favor the production of monoalkanolamine. For methods applicable in the conversion of the olefin oxide into the alkanolamine, reference may be made to, for example U.S. Pat. No. 4,845,296, which is incorporated herein by reference.

The 1,2-diol and the 1,2-diol ether may be used in a large variety of industrial applications, for example in the fields of food, beverages, tobacco, cosmetics, thermoplastic polymers, curable resin systems, detergents, heat transfer systems, etc. The alkanolamine may be used, for example, in the treating ("sweetening") of natural gas.

Unless specified otherwise, the organic compounds mentioned herein, for example the olefins, 1,2-diols, 1,2-diol ethers, alkanolamines, organic nitrogen compounds, and organic halides, have typically at most 40 carbon atoms, more typically at most 20 carbon atoms, in particular at most 10 carbon atoms, more in particular at most 6 carbon atoms. As defined herein, ranges for numbers of carbon atoms (i.e., carbon number) include the numbers specified for the limits of the ranges.

Having generally described the invention, a further understanding may be obtained by reference to the following example, which is provided for purposes of illustration only and is not intended to be limiting unless otherwise specified.

EXAMPLE 1

A calcium acetate impregnating solution can be made by dissolving 28.28 grams of calcium acetate in 165.0 grams of distilled water. 100 grams of a gamma alumina cut into individual cylindrical formed bodies is evacuated to 20 mm Hg for 1 minute and the calcium acetate impregnating solution is then added to the gamma alumina while under vacuum. The vacuum is then released and the transition alumina allowed to contact the liquid for 3 minutes. The impregnated transition alumina would then be centrifuged at 500 rpm for 2 minutes to remove excess liquid. The calcium acetate impregnated transition alumina pellets is then dried in flowing nitrogen at 110° C. for 16 hours.

An ammonium fluoride impregnation solution can be made by dissolving 19.965 grams of ammonium fluoride in 165 grams of distilled water.

The calcium acetate impregnated transition alumina can be evacuated to 20 mm Hg for 1 minute and the ammonium fluoride impregnating solution can be added to the transition alumina while under vacuum. The vacuum is then released and the transition alumina allowed to contact the liquid for 3 minutes. The impregnated transition alumina is then centrifuged at 500 rpm for 2 minutes to remove excess liquid. Impregnated transition alumina pellets are then dried in flowing nitrogen at 120° C. for 16 hours.

The dried impregnated transition alumina is then placed in a first high temperature alumina crucible. Approximately 50 g of calcium oxide is placed in a second high temperature alumina crucible. The high temperature alumina crucible containing the impregnated transition alumina is placed into the second high temperature alumina crucible, which contains the calcium oxide, and is then covered with a third high temperature alumina crucible of smaller diameter than the second crucible, such that the impregnated transition alumina is locked in by the third crucible and the calcium oxide. This assembly is then placed into a furnace at room temperature. The temperature of the furnace is increased from room temperature to 800° C. over a period of 30 minutes. The assembly is then held at 800° C. for 30 minutes and thereafter heated to 1,200° C. over a period of 1 hour. The assembly is then held at 1,200° C. for 1 hour. The furnace is then allowed to cool and the alumina is removed from the assembly.

The resultant carrier can then be tested for crush strength or attrition resistance using respectively ASTM D6175-03 or ASTM D4058-96, as described herein, or some other methods for measuring crush strength or attrition resistance. The results can be compared to those of different carriers prepared using different amounts of calcium acetate, different strength-enhancing additives, or no strength-enhancing additives. Thus, a carrier having incorporated therein a strength-enhancing amount of a strength-enhancing additive can be obtained. This carrier can then be used to prepare an olefin epoxidation catalyst, which can then be used in a process for the production of an olefin oxide, and subsequently a 1,2-diol, a 1,2-diol ether or an alkanolamine.

We claim:

1. A process for preparing a catalyst for the epoxidation of an olefin comprising:
   incorporating a fluoride-containing species and a strength-enhancing additive into a carrier;
   calcining the carrier at a temperature in the range of from greater than 900° C. to less than 1200° C.; and
   subsequently depositing a catalytic species onto the carrier wherein the strength-enhancing additive is selected from the group consisting of a zirconium species, a lanthanide Group species, inorganic glass, and mixtures thereof.

2. The process as claimed in claim 1, wherein the strength-enhancing additive comprises cerium.

3. The process as claimed in claim 1, wherein the carrier comprises alpha-alumina.

4. The process as claimed in claim 1, wherein the catalytic species comprises one or more of silver, molybdenum, nickel, and tungsten.

5. The process as claimed in claim 4, wherein the catalytic species comprises silver.

6. The process as claimed in claim 5, wherein the process additionally comprises depositing a high selectivity dopant onto the carrier.

7. The process as claimed in claim 5, wherein the process additionally comprises depositing a Group IA metal component onto the carrier.

8. The process as claimed in claim 6, wherein the process additionally comprises depositing a rhenium component, or a rhenium component and a rhenium co-promoter onto the carrier.

9. A process for preparing a catalyst for the epoxidation of an olefin comprising:
   incorporating a fluoride-containing species and cerium into a carrier;
   calcining the carrier at a temperature in the range of from greater than 900° C. to less than 1200° C.; and
   subsequently depositing a catalytic species onto the carrier.

10. The process as claimed in claim 9, wherein the carrier comprises alpha-alumina.

11. The process as claimed in claim 9, wherein the catalytic species comprises one or more of silver, molybdenum, nickel, and tungsten.

12. The process as claimed in claim 9, wherein the catalytic species comprises silver.

13. The process as claimed in claim 12, wherein the process additionally comprises depositing a high selectivity dopant onto the carrier.

14. The process as claimed in claim 12, wherein the process additionally comprises depositing a Group IA metal component onto the carrier.

15. The process as claimed in claim 9, wherein the process additionally comprises depositing a rhenium component, or a rhenium component and a rhenium co-promoter onto the carrier.

16. A process for preparing a catalyst for the epoxidation of an olefin comprising:
   incorporating a fluoride-containing species and a strength-enhancing additive into a carrier;
   calcining the carrier at a temperature in the range of from greater than 900° C. to less than 1200° C.; and
   subsequently depositing silver and a rhenium component or a rhenium component and a rhenium co-promoter onto the carrier wherein the strength-enhancing additive is selected from the group consisting of a zirconium species, a lanthanide Group species, a calcium species, a magnesium species, inorganic glass, and mixtures thereof.

17. The process as claimed in claim 16, wherein the strength-enhancing additive comprises cerium.

18. The process as claimed in claim 16, wherein the carrier comprises alpha-alumina.

19. The process as claimed in claim 16, wherein the process additionally comprises depositing a Group IA metal component onto the carrier.

* * * * *